United States Patent [19]

Huang

[11] Patent Number: 5,445,161
[45] Date of Patent: Aug. 29, 1995

[54] APPARATUS AND METHOD FOR CAPNOGRAPHY-ASSISTED ENDOTRACHEAL INTUBATION

[76] Inventor: K. C. Huang, 1000 Kensington Rd., Grosse Pointe Park, Mich. 48230

[21] Appl. No.: 134,110

[22] Filed: Oct. 8, 1993

[51] Int. Cl.⁶ .................................................. A61B 5/00
[52] U.S. Cl. ...................................... 128/719; 128/10
[58] Field of Search ............... 128/10, 11, 657, 772, 128/719, 205.28

[56] References Cited

U.S. PATENT DOCUMENTS

| | | |
|---|---|---|
| 4,011,859 | 3/1977 | Frankenberger . |
| 4,344,436 | 8/1982 | Kubota .................. 128/773 |
| 4,648,396 | 3/1987 | Raemer ................. 128/664 |
| 4,677,987 | 7/1987 | Choksi .................. 128/719 |
| 4,691,701 | 9/1987 | Williams . |
| 4,728,499 | 3/1988 | Fehder .................... 422/56 |
| 4,790,327 | 12/1988 | Despotis ................ 128/719 |
| 4,879,999 | 11/1989 | Lieman et al. ......... 128/419 |
| 4,955,946 | 9/1990 | Mount et al. .......... 128/719 |
| 5,005,572 | 4/1991 | Raemer et al. ........ 128/768 |
| 5,095,900 | 3/1992 | Fertig et al. ........... 128/719 |
| 5,124,129 | 6/1992 | Riccitelli et al. ...... 128/719 |
| 5,188,111 | 2/1993 | Yates et al. ............ 128/657 |
| 5,197,464 | 3/1993 | Babb et al. ......... 128/207.14 |
| 5,203,320 | 4/1993 | Augustine ............... 128/10 |
| 5,257,636 | 11/1993 | White ..................... 128/772 |
| 5,293,875 | 3/1994 | Stone ..................... 128/719 |
| 5,327,881 | 7/1994 | Green ....................... 128/10 |

*Primary Examiner*—Max Hindenburg
*Attorney, Agent, or Firm*—Middleton & Reutlinger; James R. Higgins, Jr.

[57] ABSTRACT

Apparatus and method for securing an airway of a patient using gas capnography. Multiple gas-aspirating conduits are included upon a flexible and steerable tube or stylet. The conduits transport gases including carbon dioxide ($CO_2$) exhaled from the airway (trachea) of a patient. The concentration or strength of the $CO_2$ transported through each conduit is analyzed and converted into a graphic display (capnograms) on the monitor of a personal computer. When the stylet is in the main stream of the gas path emitting from the patient's trachea, the $CO_2$ reading for the capnograms relative to each conduit will be substantially equal. Manipulating the flexible stylet to maintain substantial identity of the capnograms provides a guide to the location of the patient's trachea. Once the stylet is guided into the trachea, an endotracheal tube can be slipped over the stylet in the usual manner and intubation thereafter accomplished to gain control of the patient's airway.

13 Claims, 1 Drawing Sheet

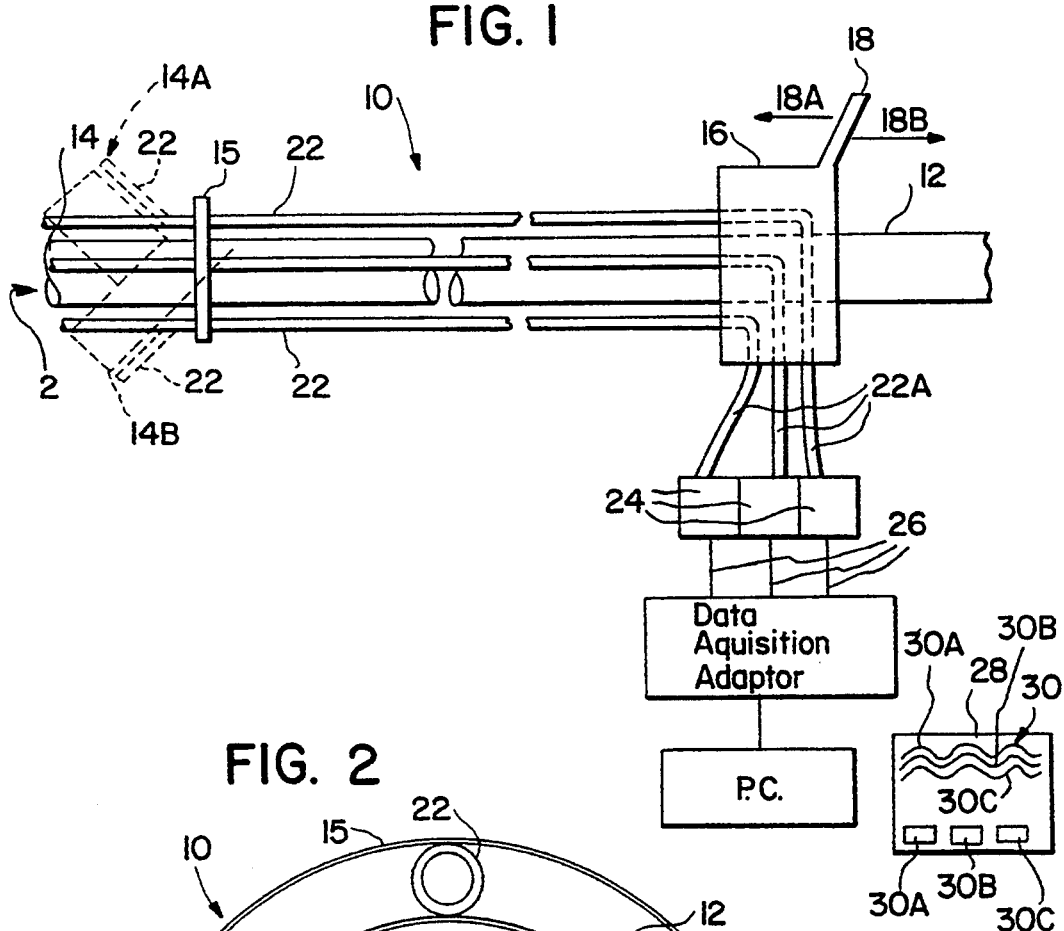
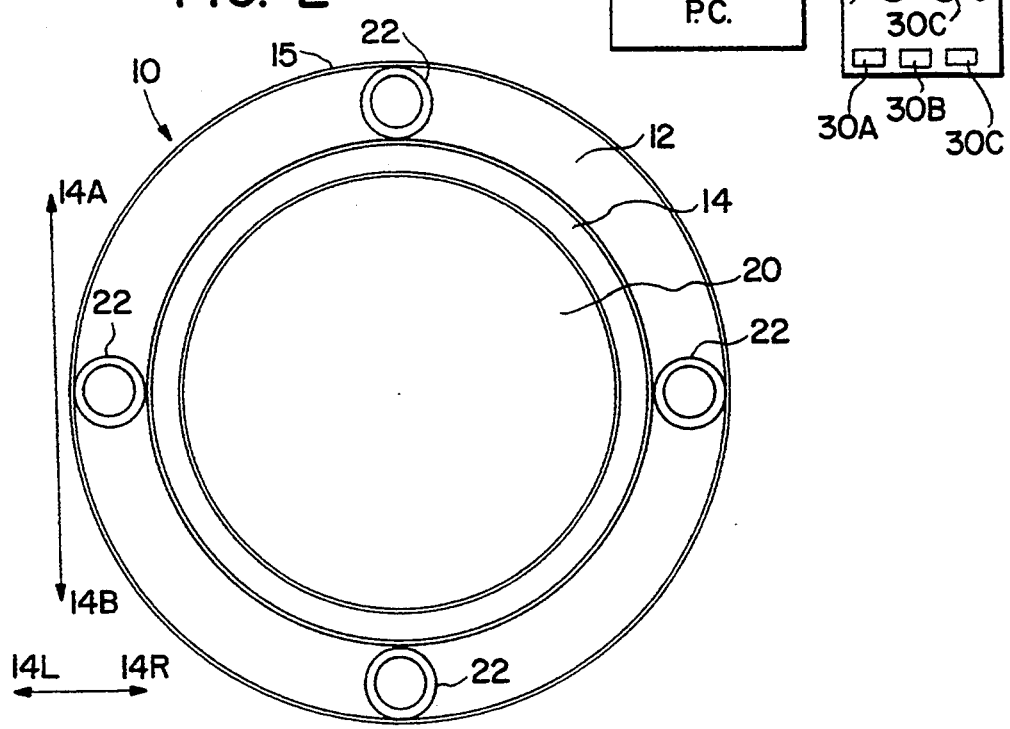

APPARATUS AND METHOD FOR CAPNOGRAPHY-ASSISTED ENDOTRACHEAL INTUBATION

BACKGROUND OF THE INVENTION

1. Field of the Invention

The present invention relates to an apparatus and method for accurately securing an airway for the purposes of endotracheal intubation of a patient. The apparatus includes a flexible, directionally steerable probe having multiple gas-aspirating ports connected to a like number of infra red gas analyzers which are in turn graphically displayed on a monitor of an available desk or personal computer ("PC") as wave-forms (or "capnograms") indicative of the strength or concentration of the analyzed gas. The gas usually analyzed is carbon dioxide ($CO_2$) which, of course, is the dominant gas from normal respiration exhaled through a patient's airway. By comparing the relative strength of the $CO_2$ wave forms/capnograms, the operator can steer the flexible probe in the direction of the dominant concentration of $CO_2$ and thereby accurately locate and secure the patient's airway.

2. Background of the Invention

More particularly, the apparatus of the present invention is a capnography assisted stylet for endotracheal intubation to secure an airway.

In medical terminology the term "airway" has two somewhat different meanings. When we talk about an airway as a device, we meant a short piece of pipe inserted into the mouth or nose and its purpose is to by-pass the tongue which can flop down and partially or even totally obstruct ventilation. These devices are only partial airways and they usually are disposable and of very little cost since it is generally a piece of inexpensive molded plastic or rubber.

The medical field also frequently talks about "gaining control of the airway" or "losing the airway." When "airway" is used in this fashion, what is meant is the ability to pass a tube from the outside all the way into the trachea. In adults, this would include the additional act or step of inflating a balloon to form a seal between the outer wall of the tube and the tracheal wall so that there is no leakage, thus allowing positive pressure ventilation and preventing the entry of undesired matters, such as gastric acid, into the airway. Tracheostomy is one way of controlling the airway, but it is usually done only in emergencies when there is insufficient time for less traumatic or invasive means (e.g., otherwise the patient may die).

To "lose the airway" means that (1) it is not possible to place the tube in the trachea and (2) the patient cannot breathe, either because something is obstructing their air passage or because of some physiologic event such as muscle paralysis or central nervous disorder or brain damage. If the patient cannot breathe and you cannot artificially breathe for him, then it is said you have lost control of the airway.

Endotracheal intubation is usually performed by anesthetists (doctors or nurses) because they do it everyday and are generally the most experienced in endotracheal intubation. It is also performed by paramedics and emergency room personnel when they feel that the patient is about to lose the airway and there are no anesthetists available. In most patients, under controlled (e.g., elective) conditions, the airway can be secured (intubated) fairly easily. However, in about five percent (5.0%) of cases, control of the airway can be difficult to gain or achieve, either because of unusual airway anatomy of the patient or the anatomy is distorted by trauma (e.g., a cancerous growth or other pathologic obstruction). Also, in some situations it is not prudent to manipulate the patient's neck for intubation. For example, if a patient has cervical spine injury and has a neck collar on, when one attempts to extend the patient's neck, there is a greatly increased risk of further damage to the spinal cord.

When all else fails, an emergency tracheostomy will have to be performed or the patient will lose the airway, interrupting breathing and resulting in serious consequences or even possibly death. Virtually all anesthesia departments in this country have some kind of "difficult airway cart" containing various devices to help gain control of a difficult airway. A frequently used device is the fiber-optic bronchoscope that permits the operator to visually "navigate" the airway and lead to the trachea to slip an endotracheal tube therein for intubation. There are many shortcomings of such fiber-optic scopes: they use coherent fibers and thus are quite expensive; they are difficult to operate and not all anesthesia personnel are trained in their use; the fibers have a tendency to break after use; the fiber optic lens can get dislocated requiring high repair costs; and sometimes secretion and blood in the airway can totally obscure the visual field.

Another method (frequently discussed but in my experience almost never used) is retrograde intubation. A hole is punctured at the neck into the trachea and a long wire is passed back into the mouth. One end of the wire is anchored at the neck and the other is pulled out the mouth and an endotracheal tube is slipped over it into the trachea. Even this seemingly direct technique can result in "hang ups" in an abnormal airway. Further, proper use of this device is often time-consuming, and if one is going to devote significant time using this device, it is often more expedient to perform a tracheostomy and gain control of the airway much more quickly.

One further method is trans-tracheal jet ventilation. In this procedure, the patient's neck is punctured and a small tube is inserted into the trachea. This tube allows a high pressure jet stream of oxygen to be delivered to the lungs. At that point, however, the airway is only partially secured and often the principal result obtained by using this device is to gain additional time to insert a proper endotracheal tube. In my practice, I use this technique frequently for difficult airways. However, the availability of approved trans-tracheal jet ventilation devices is problematic. There is a manual jet, called Sander's jet, that is nothing more than a hand operated air valve which is very difficult to operate at the rate needed for effective intubation (over 120 breaths per minute).

Finally, it is appropriate in this background section to mention intubating stylets. An intubating stylet is a long malleable rod which the anesthetist molds into a form predicted to conform to the shape of the patient's airway. After molding the stylet into the predicted shape, the anesthetist then inserts the formed stylet through the patient's mouth hoping that it will be directed to the trachea. Of course, this is often nothing more than a blind insertion and if the stylet has not been molded into a conforming shape, it will not be operationally successful. In this situation, the stylet must be withdrawn, remolded and reinserted until the trachea is located. Given that a difficult airway is almost by definition one that does not conform to a normal anatomy, this method is often futile. Nevertheless, the prior art shows much activity in trying to improve this type of device.

SUMMARY OF THE PRESENT INVENTION

The present invention is directed to an apparatus and method for controlling the difficult airway, which I have termed Capnography Assisted Stylet for Endotracheal Intubation (sometimes referred to as, "CASEI"). CASEI is quite easy to use, incorporating non-complex automation utilizing well known technology (for example, $CO_2$ capnography, graphic display on PC monitors, and the like). As a result, the present invention can be used for difficult airways and since it is so easy to use, it can also be used on easy airways.

The present invention capitalizes on the presence of carbon dioxide in the exhaling airstream from the trachea as a way to confirm the location of the trachea. Since most $CO_2$ leaves the body from the lungs via the mouth or the nose, the presence and concentration of $CO_2$ within that exhalent pathway is used as a "guide" for trachea location for endotracheal intubation.

Of course, the stream of exhaled $CO_2$ comprising the "guide" has no defined "walls," so the airway cannot be physically defined. The apparatus of the present invention solves this problem by using multiple gas-aspirating ports upon a flexible intubating stylet or specially manufactured endotracheal tubes. By using multiple ports, the apparatus including means to generate appropriate capnographs has the capacity to detect deviations in $CO_2$ concentration, which in turn will be indicative of the path to the airway. In using the present invention, the operator can then study the capnographs which detect the relative concentration of $CO_2$. For example, when the capnograph indicates a lesser relative concentration of $CO_2$, this indicates that a particular port is getting out of the gas stream leading to the airway. In a sense, the operator gets the feeling of hitting a virtual or non-physical "wall." When this occurs, the operator can redirect the stylet back into the correct path (e.g., in the direction where the capnographs are more relatively consistent with each other in their $CO_2$ concentration).

It is, of course, known to use $CO_2$ as a guide to the use of respiration devices. However, it is also known that the concentration of $CO_2$, and hence signal strength of $CO_2$-sensing devices, varies widely in respiration that can be due to many factors other than deviation. Thus, $CO_2$ concentration by itself is not a reliable indicator of the location of the airway. The present invention solves this problem by using multiple aspirating ports to sense the concentration of $CO_2$ at a plurality of locations. Properly located, these locations define the area through which the $CO_2$ is flowing (or is attempting to flow) from the airway. By directing the stylet or the endotracheal tube to maintain a relative balance of the concentration of the $CO_2$, the tip of the device will be substantially maintained within the path leading to the airway. The apparatus and method of the present invention results in a repeatable and reliable apparatus using $CO_2$ capnography to secure the airway.

More particularly, the present invention comprises an apparatus for capnography—assisted endotracheal intubation comprising: a flexible and steerable intubating tube having a moveable distal end; at least one conduit mounted along the said intubating tube, said conduit having one end movable with said distal end and an opposite end in flow communicating with means to analyze a selected gas in a gas stream; means to analyze said selected gas; means to display flow concentrations of said selected gas in response to analysis of same; and means to steer said distal end of said intubating tube.

BRIEF DESCRIPTION OF THE DRAWINGS

A better understanding of the invention will be had upon reference to the following description in conjunction with the accompanying drawings in which like numerals refer to like parts and wherein:

FIG. 1 is a schematic representation of the present invention; and

FIG. 2 is an end view of the distal end of the present invention, viewing as indicated by the numeral 2 from the left, distal, end of FIG. 1.

DESCRIPTION OF THE PREFERRED EMBODIMENT

Referring now to FIG. 1, there is presented a capnography assisted stylet for endotracheal intubation 10 in the form of a flexible and steerable intubating tube or stylet 12 having a distal end 14. I have found, in practicing the invention of CASEI, that use of a disposable flexible ureteroscope provides an acceptable stylet. It is also realized that a fiber-optic bronchoscope or an endotracheal tube with the ability to steer with the aspirating conducts may be used as the tube 12 as well. The ureteroscope (or bronchoscope, or other forms of intubating stylet) 12 is provided with an internal irrigation conduit 20 and a distal tip 14 that can be manipulated on both the x and y-axis, only the y-axis movement being shown in FIG. 1. A ring support 15 is provided adjacent to and upstream of the distal end 14 to both support and hold conduits 22 adjacent to tube 12. Ring support 15 is provided with a preselected number of openings of preselected cross-sectional area for receipt of conduits 22 therethrough. Centrally disposed within ring support 15 is also an opening sized to receive the tube 12 therethrough. Ring support 15 is positioned to maintain conduits 22 in a preselected relationship with tube 12 as the distal end is moved or manipulated. This is accomplished via known steering linkage 16 and lever 18. When lever 18 of linkage 16 is manipulated in the direction of arrows 18A/18B, this causes the distal end 14 of ureteroscope 12 to move correspondingly, as shown by the dotted line outlines of distal tip 14A or 14B. Moreover, as best shown in FIG. 2, distal end 14 may also be movable on the x-axis (14L→14R as well as the y-axis (14A→14B).

The CASEI is provided with a plurality of conduits 22 spaced around tube 12. Preferably, the selected conduits 22 will be such that, circumferentially spaced apart from one another at about 120 degrees at least three ports are available for aspirating lung gases. The proximal ends 22a of conduits 22 are connected to a like number of infra-red $CO_2$ analyzers (capnographs) 24 whose analog outputs 26 are connected to a PC. One preferred apparatus is an IBM Data Acquisition Adaptor inside an IBM-compatible personal computer, but it is realized there are a myriad of PC adaptions that will provide acceptable results. A suitable program can be written for converting the analog or digital output of the capnographs 24 into graphic displays presentable on the PC monitor 28, which in turn displays the multiple $CO_2$ wave forms (capnograms) 30 in real time. Furthermore, it has been found useful to assign a different color to each capnogram identified with each gas-aspirating port 30A, 30B, 30C. This permits the anesthetist to readily identify the individual conduits 22 which in turn is identified to a particular gas aspirating port upon distal tip 14 of scope 12. Of course, other indicia other than color may be used to differentiate the particular capnograms.

In FIG. 1, there is shown three gas-aspirating conduits 22, but a number other than three may be used for more detail (for example, FIG. 2 shows a total of four conduits 22 attached to uretereoscope 12).

To use CASEI, the operator introduces the distal end 14 from the mouth or from a nares and advances towards the trachea while observing the capnograms 30A, 30B, 30C on the heads-up display monitor 28. Initially the three tracings 30A, 30B, 30C will be nearly identical. If the tip 14 of CASEI remains in the path towards the trachea, while being advanced forward, then the capnograms 30A, 30B, 30C should remain substantially identical. However, should the tip 14 start to deviate from the ideal path, one or more capnograms 30A, 30B or 30C will start to show a $CO_2$ level deviating from a selected level or differentiation from the other capnograms. At that point one of two preferred operations can be done: [1] manually pull the lever 18 so that the tip 14 is toward the side with the largest capnograph until all three capnograms are substantially equal again; or [2] use an electromechanical actuator (not shown), such as the servo used in radio controlled model airplanes, to automatically perform the course correction. It is realized that there are other known means usable for correction of the distal end 14.

When the strength of a particular capnogram falls off or declines, which is indicative of a drop in $CO_2$ concentration, this in turn is indicative of that particular portion of the distal tip 14 getting out of the main gas stream leading to the trachea. By looking at the color or other indicia of the capnograms 30A, 30B or 30C or other $CO_2$ concentration-indicating tracing, it is possible to determine whether the tip 14 is too high or too low with respect to the gas stream emitting from the tracheal opening. By using steering lever 18 in direction 18A/18B, the operator can manipulate the tip 14 in the proper direction 14A/14B to location 14a/14b until the capnograms 30A, 30B, 30C are substantially equal again.

While I have just described manual course correction of distal tip 14, such course correction can be automated by using a variety of known electro-mechanical actuators. A servo from a radio controlled model airplane has been successfully used. With such devices, it is well within the skill of the art to create control programs to automate the course correction. For example, I have used a simple program that utilized an error signal from the capnograms to drive the servo which in turn manipulates the lever 18 until the signals for capnograms 30A, 30B, 30C are substantially equal and there is no further error signal.

Once the tip 14 has entered the trachea, an endotracheal tube can be easily slipped over the stylet 12 in the usual manner.

In my experience, what makes CASEI device different (and better) than the fiber-optic bronchoscope, is the presence of real time visual indication at all times and the ability to make course corrections based on the visual indication. The bronchoscope relies on direct vision which can be blurred by secretion and blood. Operation of CASEI, on the other hand, is not impaired or affected by secretions or blood, because the infra-red analyzers can be provided with known relatively powerful suction pumps (e.g., 300 ml per minute), not shown, for aspiration of exhaust gases. Such pumps can also clear the airstream field of the undesired liquids which create so much obstruction for a bronchoscope.

While I have described a preferred CASEI, it will be apparent to those skilled in that art that further refinements can be made to CASEI without departing from the scope and spirit of my invention. For example, it is possible to (1) add two or more gas-sensing conduits 22, one to left and one to the right (as shown in FIG. 2), so that the operator can also make corrections for deviations from midline. This would require steering linkage (not shown) to provide movement in two different planes, up/down and left/right. This modification would be useful in situations where cancer or other pathological growth has pushed the tracheal opening off center. And, it is possible to (2) add an extra servo controller (not shown) to move the scope 12 in and out; in this way the intubation becomes completely automatic. Another avenue of future interest is to provide $CO_2$ sensing abilities onto a fiber-optic bronchoscope. This will provide two independent means of assessing where you are going to locate the airway.

The foregoing detailed description is given primarily for clearness of understanding and no unnecessary limitations are to be understood therefrom, for modifications will become obvious to those skilled in the art upon reading this disclosure and may be made without departing from the spirit of the invention or the scope of the appended claims.

What is claimed is:

1. An apparatus for capnography-assisted endotracheal intubation comprising:
    a flexible and steerable intubating tube having a movable distal end;
    at least three gas aspirating ports positioned around the distal end of the intubation tube in a vertical plane, said ports having one end movable with said distal end and an opposite end in flow communicating means with means to analyze $CO_2$ concentrations in a gas stream; means to analyze said $CO_2$ concentrations;
    means to display flow concentrations of said $CO_2$ concentrations in response to analysis of same; and,
    means to steer said distal end of said intubating tube.

2. The apparatus of claim 1, said intubating tube having an internal irrigation conduit disposed therein.

3. The apparatus of claim 1, wherein said means to steer said distal end of said intubating tube is a steering linkage having one end connected to said moveable distal end of said intubating tube and the other end connected to a manually operated lever for manipulating said tip in the x-axis or y-axis.

4. The apparatus of claim 1, wherein said means to steer said distal end of said intubating tube is a steering linkage having one end connected to said moveable distal end of said intubating tube and the other end connected to an electromechanical actuator for manipulating said tip in the x-axis or y-axis.

5. The apparatus of claim 1, including electromechanical means to extend and withdraw said intubating tube.

6. The apparatus of claim 1, including a suction pump for aspiration of exhaust gases and undesired liquids from the airstream field.

7. The apparatus of claim 6, wherein said suction pump is capable of pumping at least 300 milliliters per minute.

8. The apparatus of claim 1, including at least four gas aspiration ports therein for making corrections for deviations from a midline and providing movement in up, down, right and left directions.

9. The apparatus of claim 1, including a ring support positioned upstream and adjacent to said distal end of said intubating tube to support and hold said at least three gas aspirating ports adjacent to said intubating tube.

10. The apparatus of claim 9, said ring support having a plurality of openings therein.

11. The apparatus of claim 9, wherein said ring support being positionable for maintaining said gas aspirating ports in a preselected relationship within said intubated tube during manipulation of the distal ends of said intubating tube.

12. The apparatus of claim 1, wherein said means to analyze said selected gas and means to display flow concentrations of said selected gas in response to analysis of same, comprises an infrared $CO_2$ analyzer for each gas aspirating port, each one having an analog output connected to a computer and conversion of said analog outputs of said infrared $CO_2$ analyzers into graphic display of multiple $CO_2$ wave forms in real time, and providing indicia to differentiate the particular infrared $CO_2$ analyzers outputs.

13. The apparatus of claim 12, wherein said indicia is color.

* * * * *